United States Patent
Halpern et al.

(10) Patent No.: US 10,811,138 B1
(45) Date of Patent: Oct. 20, 2020

(54) PARAMETER SELECTION MODEL USING IMAGE ANALYSIS

(71) Applicant: MEMORIAL SLOAN KETTERING CANCER CENTER, New York, NY (US)

(72) Inventors: Allan C. Halpern, New York, NY (US); Steven Q. Wang, New York, NY (US); Douglas Comrie Canfield, Short Hills, NJ (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/816,213

(22) Filed: Mar. 11, 2020

(51) Int. Cl.
| | |
|---|---|
| *G16H 50/20* | (2018.01) |
| *G16H 50/50* | (2018.01) |
| *G16H 30/20* | (2018.01) |
| *G16H 30/40* | (2018.01) |
| *G16H 20/10* | (2018.01) |
| *A61B 5/00* | (2006.01) |
| *G06T 7/00* | (2017.01) |

(52) U.S. Cl.
CPC .......... *G16H 50/20* (2018.01); *A61B 5/0013* (2013.01); *A61B 5/0077* (2013.01); *A61B 5/444* (2013.01); *A61B 5/4836* (2013.01); *A61B 5/4848* (2013.01); *G06T 7/0012* (2013.01); *G16H 20/10* (2018.01); *G16H 30/20* (2018.01); *G16H 30/40* (2018.01); *G16H 50/50* (2018.01); *A61B 2576/02* (2013.01); *G06T 2207/20081* (2013.01); *G06T 2207/30088* (2013.01); *G06T 2207/30096* (2013.01)

(58) Field of Classification Search
CPC ..................................................... G16H 50/20
See application file for complete search history.

(56) References Cited

U.S. PATENT DOCUMENTS

| | | | | |
|---|---|---|---|---|
| 8,548,828 | B1 * | 10/2013 | Longmire | G06Q 10/10 705/3 |
| 10,650,929 | B1 * | 5/2020 | Beck | G16H 50/50 |
| 2001/0032099 | A1 * | 10/2001 | Joao | G06F 19/3481 705/2 |
| 2010/0088264 | A1 * | 4/2010 | Teverovskiy | G16H 50/20 706/46 |
| 2010/0177950 | A1 * | 7/2010 | Donovan | G16H 50/30 382/133 |

(Continued)

*Primary Examiner* — Gandhi Thirugnanam
(74) *Attorney, Agent, or Firm* — Foley & Lardner LLP

(57) ABSTRACT

Described herein are systems and methods of selecting treatment parameters values for treating skin lesions. A device may establish a treatment parameter selection model using a training dataset. The training dataset may include a plurality of examples. Each example may include a sample image of an example skin lesion to which a treatment is administered using an applicator. Each example may include a first label indicating success or failure of the treatment. Each example may include a second label corresponding to treatment parameters defining the treatment. The device may identify an input image. The device may determine that the input image corresponds to a skin lesion based on visual characteristics of the input image. The device may apply the treatment parameter selection model to the input image to output a recommended treatment to apply. The device may store an association between the input image and the recommended treatment.

19 Claims, 7 Drawing Sheets

(56) References Cited

U.S. PATENT DOCUMENTS

| | | | |
|---|---|---|---|
| 2013/0322711 A1* | 12/2013 | Schultz | A61B 5/445 |
| | | | 382/128 |
| 2014/0094642 A1* | 4/2014 | Fuji | A61N 5/103 |
| | | | 600/1 |
| 2017/0228514 A1* | 8/2017 | Apte | G06F 19/3418 |
| 2018/0333105 A1* | 11/2018 | Hayat | G06T 7/277 |
| 2019/0189247 A1* | 6/2019 | Iyer | G16C 20/30 |
| 2019/0392953 A1* | 12/2019 | Steuer | G06T 7/0012 |
| 2020/0060603 A1* | 2/2020 | Bower | A61B 5/6868 |
| 2020/0075148 A1* | 3/2020 | Nguyen | G06N 3/04 |

\* cited by examiner

PARAMETER SELECTION MODEL USING IMAGE ANALYSIS

BACKGROUND

Image analysis is used to analyze images to identify certain features within an image. Various image analysis techniques can be used to detect such features. Upon detecting such features, appropriate actions can be performed on the objects based on the detection.

SUMMARY

The human skin is comprised of a number of layers to protect underlying internal organs, muscles, bones, and ligaments of the human body. A cutaneous condition may form on one of the layers of the skin. Dermatoscopy or a biopsy may be performed to examine the condition formed on the human skin of a subject.

Within the human body, the layers forming the skin may include: the epidermis, dermis, and subcutaneous tissue. The epidermis may correspond to the outermost layer of skin. The dermis may correspond a layer of skin beneath the epidermis. The subcutaneous tissue may correspond to the lowermost layer connecting the skin to the bone and muscle. One type of cutaneous condition affecting the subject may include a skin lesion on the epidermis. For example, as the human skin ages, a benign skin tumor referred to seborrheic keratosis (SK) may form along the outer surface of the skin. Such lesions may be elevated with a round or ovular shape, and may be discolored relative to the surrounding skin.

One approach to identify such skin lesions may include having a medical professional perform a dermatoscopy using a light source to illuminate a region along the outer surface of the skin. Another approach may include a clinician or medical professional performing a skin biopsy by physically removing (e.g., using a scalpel, blade, punch, or needle) a portion of the skin lesion for examination using a microscope. Based on the examination, the clinician may determine whether the subject has the skin lesion, and may determine how to remove, alleviate, or otherwise treat the skin lesion. Both approaches, however, may involve manual inspection of the skin tissue in carrying out the diagnosis, entailing both special expertise and a very lengthy process to produce the diagnosis and determine the treatment method. In addition, the diagnosis and the treatment method determined using these techniques may suffer from inaccuracy.

To address the technical challenges arising from identifying skin lesions, feature recognition and parameter selection models may be leveraged to determine whether the skin sample contains a skin lesion and treatment parameters to apply to treat the skin lesion. The feature recognition model may be trained using example images to recognize the presence of a skin lesion (e.g., seborrheic keratosis) from an image of a skin. In addition, the treatment selection model may be trained using a sample dataset to generate treatment parameters based on the skin lesion recognized from the image. Each example in the sample dataset may include a sample image of a skin lesion and labels describing a treatment that was applied to the skin lesion. For instance, the labels may include: an indicator identifying whether the treatment was successful; application parameters (e.g., cryotherapy or liquid solution treatment); a duration of the administration of the treatment; a distance between the skin lesion and the applicator; one or more attributes of the applicator itself (e.g., a type of applicator, a size of tip, and use of a pledget); anatomic location of the skin lesion; and subject traits of the subject, among others.

Once the models are trained, an image acquisition device (e.g., a camera) may obtain an image of a region of an outer layer on a skin that contains a skin lesion from a subject (e.g., a patient or a user). The image may be fed into the feature recognition model to determine whether the image contains a skin lesion. If the image is determined to not include any skin lesions (or is determined to be insufficient quality), the user of the image acquisition device may be prompted (e.g., using a graphical user interface displayed on a client) to re-obtain the image. On the other hand, if the image is determined to include a skin lesion (and is determined to be of sufficient quality), the parameter selection model may be applied to the image. By applying, the parameter selection model may generate and output recommended treatment parameters identifying the treatment that should be applied to the skin lesion in the image. For instance, the treatment parameters may specify a modality of treatment (e.g., cryotherapy or liquid solution treatment), the duration of the administration, and the distance between the skin lesion and the applicator, among others. The parameter selection model may also output multiple recommended treatments, ranked by likelihood of success. With the output, the clinician may administer the treatment on the skin lesion of the subject.

By using these models, the reliance on special expertise diagnosis and treatment planning may be lessened or eliminated, thereby shortening the time-consuming process overall. Compared to manual inspection using dermatoscopy or skin biopsy techniques, the models may produce a more objective and accurate measure of the skin lesion diagnosis and the treatment selection. Furthermore, in making use of computing devices, the functionality of the diagnosis and treatment selection may be distributed across different devices at various locations, thereby providing greater access to more users for diagnosis and treatment of skin lesions.

At least one aspect of the present disclosure is directed to a method of selecting treatment parameters values for treating skin lesions. One or more processors may establish a treatment parameter selection model using a training dataset. The training dataset may include a plurality of examples. Each example may include a sample image of an example skin lesion to which a treatment is administered using an applicator. Each example may include a first label indicating success or failure of the treatment applied to the example skin lesion in the sample image. Each example may include a second label indicating at least one value corresponding to one or more treatment parameters defining the treatment applied to the example skin lesion. The predefined one or more treatment parameters may specify at least one of: a type of the treatment, a distance between the applicator of the treatment and the example skin lesion, or a duration of administration of the treatment on the example skin lesion. The one or more processors may identify an input image including one or more visual characteristics. The one or more processors may determine that the input image corresponds to a skin lesion based on the one or more visual characteristics of the input image. The one or more processors may apply, responsive to determining that the input image includes the skin lesion, the treatment parameter selection model to the input image to output one or more values corresponding to the one or more treatment parameters to define a recommended treatment to apply to the skin lesion corresponding to the input image. The one or more processors may store in one or more data structures, an association between the input image and the one or more values corresponding to the one or more treatment parameters to define the recommended treatment to apply to the skin lesion corresponding to the input image.

In some embodiments, the one or more processors may determine that a second input image does not include any skin lesions based on one or more second visual characteristics of the second input image. In some embodiments, the one or more processors may provide, responsive to determining that the second input image does not include any skin lesions, a message for presentation indicating that the second input image does not include any skin lesions.

In some embodiments, the one or more processors may establish a feature recognition model using a second training dataset. The second training dataset may include a first plurality of images and a second plurality of images. The first plurality of images may be identified as including at least one skin lesion. The second plurality of images may be identified as not including any skin lesions. In some embodiments, determining that the input image includes the skin lesion may further include applying the feature recognition model to the input image to determine that the input image includes the skin lesion based on the one or more visual characteristics.

In some embodiments, the one or more processors may receive a result indicating one of success or failure of the recommended treatment applied to the skin lesion included in the input image. In some embodiments, the one or more processors may update the treatment parameter selection model using the result and the one or more values corresponding to the one or more treatment parameters for the recommended treatment.

In some embodiments, at least one value outputted by the treatment parameter selection model may include a candidate distance selected from a plurality of candidate distances between the applicator of the treatment and the skin lesion. In some embodiments, at least one value outputted by the treatment parameter selection model may include a candidate duration selected from a plurality of candidate durations of administering the treatment on the skin lesion. In some embodiments, at least one value outputted by the treatment parameter selection model may include a candidate type of treatment selected from a plurality of candidate types of treatments.

In some embodiments, establishing the treatment parameter selection model may include establishing the treatment parameter selection model using the training dataset, the training dataset including the plurality of examples. Each example may include a third label identifying one or more trait characteristics of a sample subject from which the sample image including the example skin lesion is acquired.

In some embodiments, applying the treatment parameter selection model may include applying the treatment parameter selection model to the input image to output a plurality of recommended treatments to apply to the skin lesion included in the input image. Each treatment may be defined by one or more values corresponding to the one or more treatment parameters and associated with a likelihood of success of treating the skin lesion.

In some embodiments, the one or more processors may provide a message for presentation identifying the one or more values corresponding to the one or more treatment parameters for the recommended treatment to apply to the skin lesion included in the input image.

At least one aspect of the present disclosure is directed to a system for selecting treatment parameters values for treating skin lesions. The system may include one or more processors. The one or more processors may establish a treatment parameter selection model using a training dataset. The training dataset may include a plurality of examples. Each example may include a sample image of an example skin lesion to which a treatment is administered using an applicator. Each example may include a first label indicating success or failure of the treatment applied to the example skin lesion in the sample image. Each example may include a second label indicating at least one value corresponding to one or more treatment parameters defining the treatment applied to the example skin lesion. The predefined one or more treatment parameters may specify at least one of: a type of the treatment, a distance between the applicator of the treatment and the example skin lesion, or a duration of administration of the treatment on the example skin lesion. The one or more processors may identify an input image including one or more visual characteristics. The one or more processors may determine that the input image corresponds to a skin lesion based on the one or more visual characteristics of the input image. The one or more processors may apply, responsive to determining that the input image includes the skin lesion, the treatment parameter selection model to the input image to output one or more values corresponding to the one or more treatment parameters to define a recommended treatment to apply to the skin lesion corresponding to the input image. The one or more processors may store in one or more data structures, an association between the input image and the one or more values corresponding to the one or more treatment parameters to define the recommended treatment to apply to the skin lesion corresponding to the input image.

In some embodiments, the one or more processors may determine that a second input image does not include any skin lesions based on one or more second visual characteristics of the second input image. In some embodiments, the one or more processors may provide, responsive to determining that the second input image does not include any skin lesions, a message for presentation indicating that the second input image does not include any skin lesions.

In some embodiments, the one or more processors may establish a feature recognition model using a second training dataset. The second training dataset may include a first plurality of images and a second plurality of images. The first plurality of images may be identified as including at least one skin lesion. The second plurality of images may be identified as not including any skin lesions. In some embodiments, the one or more processors may apply the feature recognition model to the input image to determine that the input image includes the skin lesion based on the one or more visual characteristics.

In some embodiments, the one or more processors may receive a result indicating one of success or failure of the recommended treatment applied to the skin lesion included in the input image. In some embodiments, the one or more processors may update the treatment parameter selection model using the result and the one or more values corresponding to the one or more treatment parameters for the recommended treatment.

In some embodiments, at least one value outputted by the treatment parameter selection model may include a candidate distance selected from a plurality of candidate distances between the applicator of the treatment and the skin lesion. In some embodiments, at least one value outputted by the treatment parameter selection model may include a candidate duration selected from a plurality of candidate durations of administering the treatment on the skin lesion. In some embodiments, at least one value outputted by the treatment parameter selection model may include a candidate type of treatment selected from a plurality of candidate types of treatments.

In some embodiments, the one or more processors may establish the treatment parameter selection model using the training dataset, the training dataset including the plurality of examples. Each example may include a third label identifying one or more trait characteristics of a sample subject from which the sample image including the example skin lesion is acquired.

In some embodiments, the one or more processors may apply the treatment parameter selection model to the input image to output a plurality of recommended treatments to apply to the skin lesion included in the input image. Each treatment may be defined by one or more values corresponding to the one or more treatment parameters and associated with a likelihood of success of treating the skin lesion.

In some embodiments, the one or more processors may provide a message for presentation identifying the one or more values corresponding to the one or more treatment parameters for the recommended treatment to apply to the skin lesion included in the input image.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

Following below are more detailed descriptions of various concepts related to, and embodiments of, systems and methods for segmenting biomedical images. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes systems and methods for selecting treatment parameters values for treating skin lesions.

Section B describes a network environment and computing environment which may be useful for practicing various computing related embodiments described herein.

A. Systems and Methods Selecting Treatment Parameters Values for Treating Skin Lesions.

Figure 1:
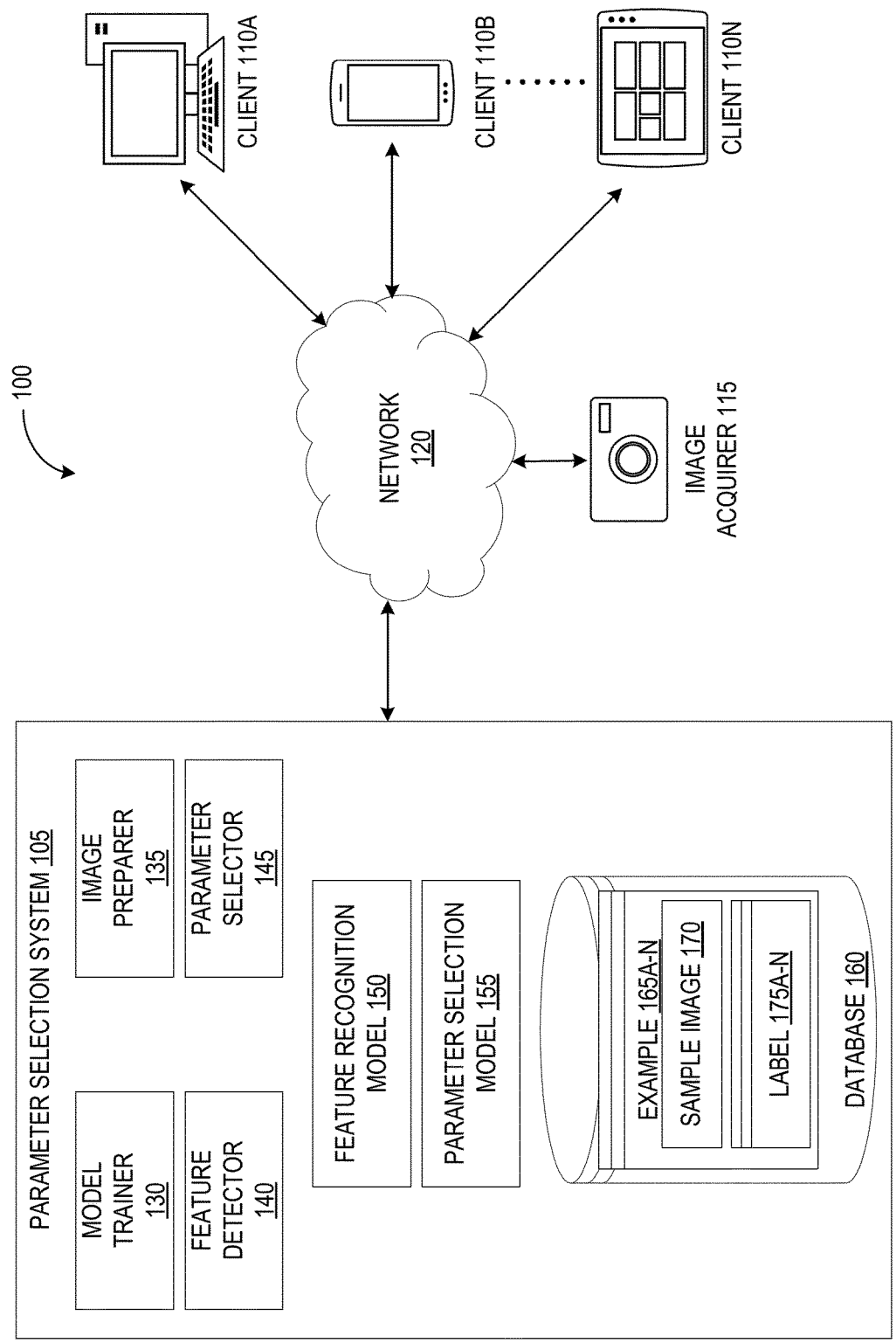
FIG. 1 depicts a block diagram of an example system for selecting treatment parameters values for treating skin lesions in accordance with an illustrative embodiment.

Referring now to FIG. 1, depicted a block diagram of a system 100 for selecting treatment parameters values for treating skin lesions. In overview, the system 100 may include at least one parameter selection system 105, one or more clients 110A-N (hereinafter generally referred to as client 110), and at least one image acquirer 115, among others. The parameter selection system 105, the clients 110, and the image acquirer 115 may be communicatively coupled with one another via at least one network 120. The parameter selection system 105 may include at least one model trainer 130, at least one image preparer 135, at least one feature detector 140, at least one parameter selector 145, at least one feature recognition model 150, and at least one parameter selection model 155, and at least one database 160, among others. The database 160 may maintain or include a set of examples 165A-N (hereinafter generally referred to as examples 165). Each example 165 may include a sample image 170 and a set of labels 175A-N. Each of the components of system 100 (e.g., the parameter selection system 105 and its components, the clients 110, the image acquirer 115, and the network 120) may be implemented using hardware or a combination hardware and software, such as those of system 500 as detailed herein in Section B.

Figure 2:
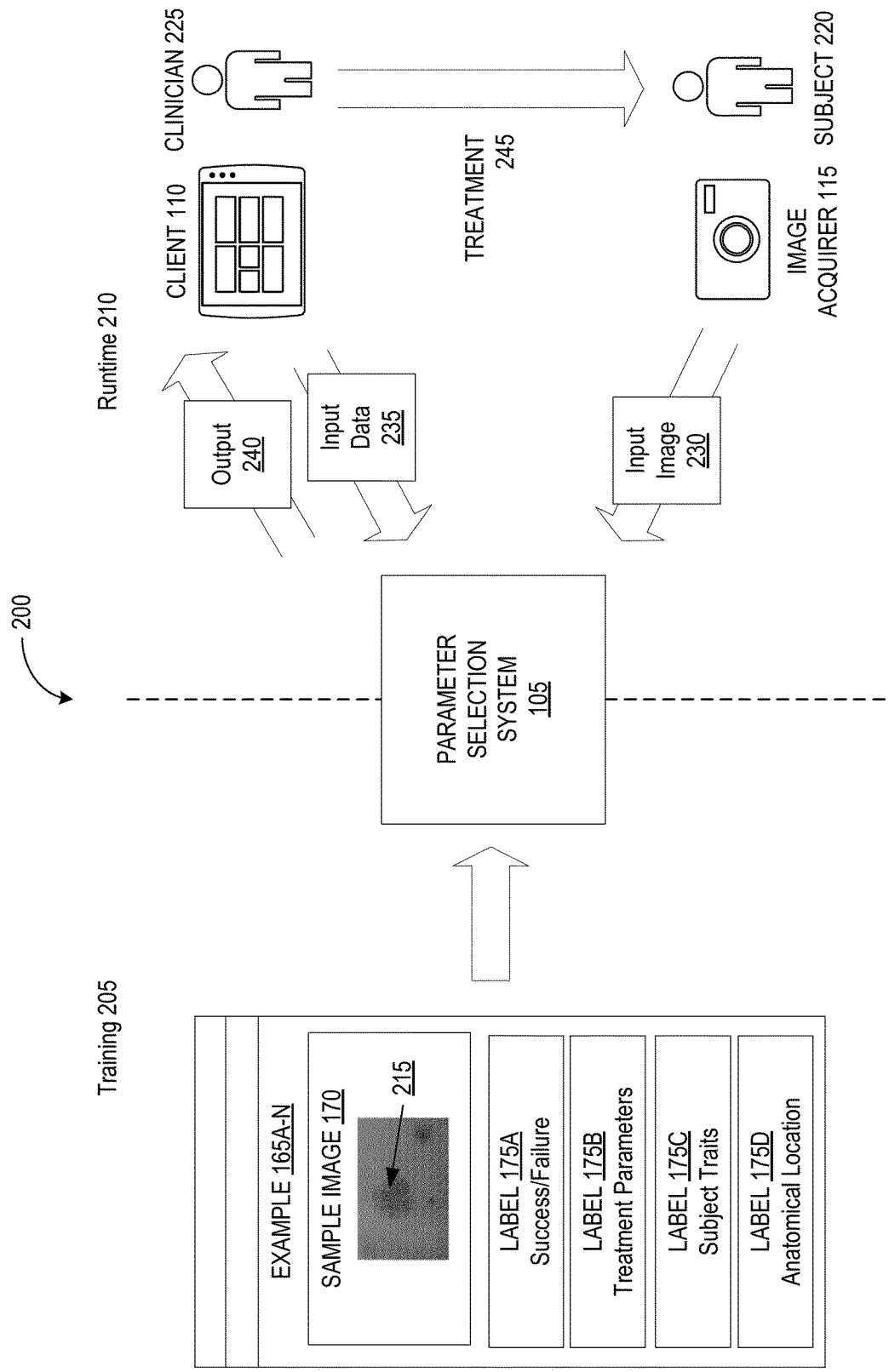
FIG. 2 depicts a sequence diagram of an example process for training a model and selecting treatment parameters values for treating skin lesions using the model in accordance with an illustrative embodiment.

Referring now to FIG. 2, depicted is a sequence diagram of a process 200 for training a model and selecting treatment parameters values for treating skin lesions using the model. In the context of system 100, the parameter selection system 105 may have and run in accordance with at least two modes of operation, training 205 and runtime 210 mode. Under training 205, the feature recognition model 150 and the parameter selection model 155 may be trained using training data on the database 160. Under runtime 210, the feature recognition model 150 and the parameter selection model 155 may be used to generate and output recommended treatments for a clinician 225 to administer to treat a skin lesion on a subject 220.

While operating in the training mode 205, the model trainer 130 executing on the parameter selection system 105 may establish the feature recognition model 150 (sometimes referred herein as a skin lesion detection model), for example, using training data stored on the database 160. The feature recognition model 150 may receive an image as an input. The feature recognition model 150 may generate a likelihood or an indication of whether the image contains a skin lesion (e.g., a seborrheic keratosis (SK)) as an output based on visual characteristics in the image as an output. In some embodiments, the feature recognition model 150 may generate a class of skin lesion as the output. In some embodiments, the output of the feature recognition model 150 may include a feedback for reacquiring the image of the skin lesion. The input and the output of the feature recognition model 150 may be related or dependent on each other via a set of weights or parameters. The feature recognition model 150 may be a machine learning model, such as a regression model (e.g., linear or logarithmic), a naïve Bayes model, a support vector machine (SVM), an artificial neural network (ANN), a k-nearest neighbor classification model, a decision tree, a discriminant analysis model, or a mixture model, among others.

The training of the feature recognition model 150 may be in accordance with supervised or unsupervised learning techniques, among others. The model trainer 130 may access the database 160 to identify the training data. The training data may include multiple sets of images. At least some of the images may be of an outermost layer of a skin acquired via an image acquisition device (e.g., a camera) from a human subject. For example, the sample images used to train the feature recognition model 150 may be acquired from human subjects with skin lesions that were previously administered treatment. Each image of the training dataset may include or may be associated with a label. The training dataset may be received from the image acquisition device involved in the previous administrations of treatment, and may be stored and maintained on a database. Each image and label may be stored and maintained as a data structure or an entry on a database. For instance, the image may be stored as a set of files and the label may be stored as metadata for the set of files.

At least one set may include images identified or labeled as containing the skin lesion. In addition, the image may identify or be labeled with the type of skin lesion. At least one set may include images identified or labeled as not containing any skin lesions. In some embodiments, the images labeled as not containing any skin lesions may be associated with a label identifying a feedback for properly reacquiring the image of the skin. For example, the feedback for the label may indicate "increase brightness," "improve focus," "lower contrast," "move camera left," or "zoom in," among others. In some embodiments, a feature space representation corresponding to the sample image may be used in training. The feature space representation may correspond to one or more visual characteristics in the image and may be derived using a transform function, such as a Fourier transform, wavelet transform, or convolution, among others.

With the identification, the model trainer 130 may feed the training data to the feature recognition model 150 for training. In training the feature recognition model 150, the model trainer 130 may identify the output of the feature recognition model 150 from feeding the sample image. The output may indicate whether the image contains a skin lesion. In some embodiments, the output may indicate a likelihood that the image contains a skin lesion. The likelihood may also indicate a quality (or an acquisition quality) of the image of the skin lesion within the entire image. In some embodiments, the output may also indicate the feedback for properly reacquiring the image of the skin. The model trainer 130 may compare the output of the feature recognition model 150 with the label that may indicate the expected outcome for the input image. From comparing, the model trainer 130 may calculate or determine an error metric for the feature recognition model 150. The error metric may correspond to an amount of deviation between the label and the output. Using the error metric, the model trainer 130 may set, adjust, or otherwise change the parameters or weights of the feature recognition model 150. The model trainer 130 may repeat the process of feeding the training data and calculation of error metrics until the training of the feature recognition model 150 is determined to be complete. For example, the model trainer 130 may continue to feed or input the training data including both sets of images into the feature recognition model 150 until the weights or parameters reach convergence.

In addition, the model trainer 130 may establish the parameter selection model 155, for example, using training data, such as the set of examples 165 maintained on the database 160. The parameter selection model 155 may include an image with a skin lesion as an input and may generate a recommended treatment as an output. The inputs and the outputs of the parameter selection model 155 may be related or dependent on one another via a set of weights or parameters. The parameter selection model 155 may be a machine learning model, such as a regression model (e.g., linear or logarithmic), a naïve Bayes model, a support vector machine (SVM), an artificial neural network (ANN), a k-nearest neighbor classification model, a decision tree, a discriminant analysis model, a mixture model, among others.

The model trainer 130 may access the database 160 to identify the set of examples 165. Each example 165 may include at least one sample image 170. The sample image 170 may be an image of an outermost layer of a skin acquired via an image acquisition device (e.g., a camera) from a human subject, and may contain or include at least one skin lesion 215 on the layer. The skin lesion 215 may include, for example as depicted, seborrheic keratosis, and may correspond to a region of the skin that is elevated and discolored relative to a surrounding area of normal skin. The skin lesion 215 may also be, for example, a macule, a papule, a plaque, a nodule, a vesicle, a bulla, a pustule, a cyst, a wheal, a tumor, ulcer, wart, fissure, maceration, and abrasion, among other types of skin conditions. In some embodiments, a feature space representation (e.g., derived via a transform function) corresponding to the sample image 170 may be used in training. In some embodiments, the sample image 170 may include metadata that define one or more regions (e.g., by coordinates) within the image 170 corresponding to the skin lesion 215.

Each example 165 for training the parameter selection model 155 may include one or more labels 175 associated with the sample image 170. As part of the examples 165, the skin lesion 215 depicted in the sample image 170 may have been obtained from the region of the outer skin of a patient that had previously undergone treatment. The labels 175 may characterize the treatment administered to the skin lesion 215 in the sample image 170 of the same example 165. For example, a clinician may have administered a treatment on an affected region of an outer skin of the patient, and used a computing device (e.g., the client 110) to store and maintain an image file corresponding to the sample image 170. The clinician may have also used the computing device to enter various parameters characterizing the skin lesion 215 (e.g., type of skin lesion), the treatment (e.g., the type and dosage of treatment and timestamp), and the results of the treatment (e.g., success or failure). In some cases, the clinician may have administered various treatments on the affected region of the patient multiple times, and each time may use the computing device to enter parameters characterizing the treatment. The computing device may subsequently send the sample image 170 and the labels 175 to the parameter selection system 105. Upon receipt, the model trainer 130 may package the sample image 170 and the one or more labels 175 as one of the examples 165 to use in training the parameter selection model 155. The model trainer 130 may store and maintain the packaged example 165 including the sample image 170 and the labels 175 as a data structure (e.g., an array, linked list, binary tree, heap, or class instantiation) or an entry on the database 165. For example, one example 165 may correspond to a data structure identifying the sample image 170 using the file pathname and containing one or more attributes for the labels 175 to the sample image 170. In some embodiments, the model trainer 130 may aggregate multiple examples 165 from various computing devices over time.

In each example 165, at least one label 175A may include a value indicating whether the treatment administered to the skin lesion 215 is successful or a failure. In some embodiments, the value of the label 175A may indicate a measure of improvement in the skin lesion 215 after the administration of the treatment. Continuing with the previous example, the clinician may examine the skin lesion 215 in the sample image 170 after the administration of the treatment, and may input whether the treatment was successful or failure for the label 175A using the computing device. At least one label 175B may include one or more values defining the parameters of the treatment applied to the skin lesion 215. The treatment parameter may specify: a type or modality of treatment such as cryotherapy (e.g., liquid nitrogen, dimethylether (DME), DME propane mixture, liquefied carbon dioxide, and liquefied nitrous oxide) or a liquid solution-based therapy (e.g., salicylic acid, hydrogen peroxide, cantharidine, imiquimod, and fluorouracil); a distance between an applicator (e.g., a tool or instrument to provide the cryotherapy or the liquid solution) of the treatment and the skin lesion 215 in the sample image 170; one or more attributes of the applicator itself (e.g., a type of applicator, a size of tip, and use of a pledget); an energy, force, or pressure to be applied via the applicator to the skin lesion 215 in administering the treatment; a time duration of the administration of the treatment; and a frequency of administration of treatment, among others. The label 175B may include any combination of parameters defining the treatment. For example, in conjunction with the administration of the treatment on the skin lesion 215, records for the administration of the treatment to the skin lesion 215 in the sample image 170 may be created or updated by the clinician or assistant to include values of the treatment values. In some embodiments, the value of at least one of the parameters in the label 175B may correspond to one of set candidate values. For example, the value of the distance, the pressure, and the time duration in the label 175B may correspond to one of a prefixed set of values (e.g., 2 cm, 5 cm, 7.5 cm, or 10 cm for distance). The prefixed set of values may be selected from a graphical user interface displayed on a computing device used to record the values of the treatment parameters defining the administration of the treatment to the skin lesion 215.

At least one label 175C may identify traits of the subject from which the sample image 170 is obtained. The traits may include, for example, age, gender, race, and a skin type (e.g., a Fitzpatrick skin phototype), among others. At least one label 175D may identify an anatomical location of the skin lesion 215 in the example 165. The anatomical location may include, for example, a head, a neck, a trunk, an upper limb, a lower limb, or a cavity, or any other portion of the human body. In some embodiments, the example 165 may include at least one label 175 identifying a class or type of the skin lesion in the sample image 170.

With the identification of the set of examples 165, the model trainer 130 may train the parameter selection model 155 using the examples 165. The training of the parameter selection model 155 may be in accordance with supervised or unsupervised learning techniques, among others. In training the parameter selection model 155, the model trainer 130 may identify the output of the parameter selection model 155 from feeding the sample image 170 of the example 165. The output may include the treatment parameters for a recommended treatment. In some embodiments, the output may also indicate a likelihood of success in treating the lesion 215 in the sample image 170 of the example 165. The model trainer 130 may compare the output of the parameter selection model 155 with the label that may indicate the expected outcome for the sample image 170 of the example 165. From comparing, the model trainer 130 may calculate or determine an error metric for the parameter selection model 155. The error metric may correspond to an amount of deviation between the label and the output. Using the error metric, the model trainer 130 may set, adjust, or otherwise change the parameters or weights of the parameter selection model 155. The model trainer 130 may repeat the process of feeding the training data and calculation of error metrics until the training of the parameter selection model 155 is determined to be complete. For example, the model trainer 130 may continue to feed or input examples 165 into the parameter selection model 155 until the weights or parameters of the model reach convergence. Upon completion of the training 205 of both the feature recognition model 150 and the parameter selection model 155, the parameter selection system 105 may run in accordance with the runtime 210 mode.

Under the runtime mode 210, the image acquirer 115 may acquire or obtain at least one image 230 of a region of an outer skin from the subject 220. The image acquirer 115 may be, for example, a camera, such as a modular camera, a camera with a cross-polarized or a parallel-polarized filter, a digital single-lens reflex camera, a charge-coupled device (CCD) image sensor, or an active-pixel sensor, among others, for obtaining the image of the region of the outer skin of the subject 220. In some embodiments, the image acquirer 115 may be part of another device or may be communicative coupled with the other device, such as one of the clients 110. For example, the image acquirer 115 may be a modular camera that is equipped on a smartphone device. The user operating the image acquirer 120 may be someone else besides the clinician 225, such as the subject 220 or another user. In some embodiments, an application running on the device (e.g., one of the clients 110) may control the obtaining of the input image 230 by the image acquirer 115. The application may interface with other components of the system 100, such as the parameter selection system 105.

The image acquirer 120 may be directed at the region of the outer skin of the subject 220 of interest. For instance, the subject 220 or another user of the image acquirer 120 may point the sensing end of the image acquirer 115 to the region of the outer skin of the subject 220. The region of the outer skin from which the image 230 is obtained may include or contain a skin lesion (e.g., seborrheic keratosis or a wart) on the subject 220. With the acquisition, the image acquirer 115 may transmit or provide the input image 230 to the parameter selection system 105. In some embodiments, the image acquirer 115 may store and maintain the input image 230 for provision to the parameter selection system 105 upon a request at a subsequent time. In some embodiments, the image acquirer 115 may identify and store metadata associated with the input image 230. The metadata may include a subject identifier for the subject 220, a device identifier for the image acquirer 115, a timestamp identifying a date and time at which the input image 230 is acquired, among others.

The image preparer 135 executing on the parameter selection system 105 may identify the input image 230 acquired via the image acquirer 115 of the region of the outer skin of the subject 220. In some embodiments, the image preparer 135 may receive the input image 230 from the image acquirer 115 subsequent to the acquisition. Upon identification, the image preparer 135 may perform pre-processing of the input image 230 for additional processing by the feature recognition model 150 or the parameter selection model 155. The pre-processing may be to standardize or regularize the input image 230 for additional processing by the parameter selection system 105. The pre-processing by the image preparer 135 may be in accordance with any number of techniques, such as resizing, de-noising, segmentation, decompression, extraction, or edge smoothing, among others. In some embodiments, the image preparer 135 may apply a transform function to convert the input image 230 into a feature space representation for the addition processing by the feature recognition model 150 or the parameter selection model 155. The transform function may include a Fourier transform, wavelet transform, or convolution, among others. The image preparer 135 may also convey or provide the input image 230 to the feature detector 140 or the parameter selector 145.

The feature detector 140 executing on the parameter selection system 105 may apply the input image 230 from the image acquirer 115 to the feature recognition model 150 to determine whether the input image 230 contains a skin lesion. In applying, the feature detector 140 may feed or provide the input image 230 as an input to the feature recognition model 150. In some embodiments, the feature detector 140 may generate a feature space representation of the input image 230 using the transform function. With the generation, the feature detector 140 may feed or provide the feature space representation to the feature recognition model 150. The feature detector 140 may apply the weights or parameters of the feature recognition model 150 to the input image 230 to generate an output from the feature recognition model 150. In some embodiments, the feature detector 140 may identify the output from the feature recognition model 150.

Based on the output from the feature recognition model 150, the feature detector 140 may determine whether the input image 230 contains any skin lesion. The output may indicate a presence or an absence of features within the image 230 correlated with or corresponding to a skin lesion. In some embodiments, the output may indicate a feedback for reacquiring the input image 230 in addition to the indication of absence. For example, the feature detector 140 may compare the input image 230 with the sample images used to train the feature recognition model 150. When the input image 230 (or the corresponding feature space representation) is determined to be closest to one of the sample images labeled as lacking the skin lesion, the feature detector 140 may select or identify the feedback for reacquiring the input image 230 assigned to the sample image. For example, the feedback may include one of the text in the label for images to train the feature recognition mode, such as: "increase brightness," "improve focus," "lower contrast," "move camera left," or "zoom in," among others. When the output indicates the presence, the feature detector 140 may determine that the input image 230 contains the skin lesion. For example, when the input image 230 (or the corresponding feature space representation) is determined to be closest to one of the sample images labeled as including a skin lesion, the feature detector 140 may determine that the input image 230 contains the skin lesion. Otherwise, when the output indicates absence, the feature detector 140 may determine that the input image 230 does not contain any skin lesion. In some embodiments, the output may indicate a likelihood that the input image 230 has features correlated with or corresponding to a skin lesion.

The feature detector 140 may compare the likelihood indicated in the output with a threshold value. The threshold value may delineate a likelihood at which to determine whether the input image 230 contains any skin lesion. In some embodiments, the likelihood may indicate a quality of the region within the input image 230 corresponding to the skin lesion, and the threshold value may delineate the quality at which to further process the input image 230. When the likelihood satisfies (e.g., is greater than) the threshold value, the feature detector 140 may determine that the input image 230 contains the skin lesion. In some embodiments, the feature detector 140 may also determine that the skin lesion in the input image 230 is of sufficient quality when the likelihood satisfies the threshold value. In some embodiments, the feature detector 140 may classify or identify a type of the skin lesion in the input image 230. On the other hand, when the likelihood does not satisfy (e.g., is less than or equal to) the threshold value, the feature detector 140 may determine that the input image 230 does not contain any skin lesion. In some embodiments, the feature detector 140 may also determine that the skin lesion in the input image 230 is of insufficient quality when the likelihood does not satisfy the threshold value.

When the input image 230 is determined to contain a skin lesion, the feature detector 140 may convey or provide the input image 230 to the parameter selection model 155 for additional processing. In some embodiments, the feature detector 140 may also store and maintain an indication that the input image 230 contains the skin lesion. Conversely, when the input image 230 is determined to not contain any skin lesions, the feature detector 140 may provide or transmit a message of the determination to the image acquirer 115 (or the device to which the image acquirer 115 is connected to) for presentation. The message may indicate that the input image 230 lacks skin lesions. The message may also indicate that the region of the outer skin of the subject 220 in the input image 230 is improperly taken or that another image 230 of the region is to be reacquired. For example, the message may include a prompt stating, "Please retake image of skin lesion." In some embodiments, the feature detector 140 may determine the feedback to provide from the feature recognition model 150, when the input image 230 is determined to not contain any skin lesions. The feedback may be generated and output by the feature recognition model 150, such as "increase brightness," "improve focus," "lower contrast," "move camera left," or "zoom in," among others. The feature detector 140 may include the feedback in the message indicating that the input image 230 lacks skin lesions. From the previous example, the message may also include a prompt with the notification, "Please zoom-in to reacquire image of the skin lesion." Upon presentation of the message (e.g., via display or speaker), the image acquirer 115 may re-acquire the input image 230 of the region of the outer skin of the subject 220, and the functionality of the image acquirer 115, the image preparer 135, and the feature detector 140 may be repeated.

The parameter selector 145 executing on the parameter selection system 105 may apply the input image 230 to the parameter selection model 155 to generate or output one or more values corresponding to treatment parameters. The input image 230 may be applied by the parameter selector 145 to the parameter selection model 155 upon the feature detector 140 determining that the input image 230 contains a skin lesion. The treatment parameters may define a recommended treatment to apply to the skin lesion on the region of the outer skin corresponding to the input image 230. In some embodiments, the parameter selector 145 may receive a request for a recommendation from one of the clients 110. The request may correspond to a command to retrieve a recommended treatment, and may include additional input data 235 to apply in conjunction with the input image 230. The input data 235 may include, for example, the subject identifier for the subject 220, the traits of the subject 220 (e.g., age, race, or Fitzpatrick skin condition), and the anatomical location from which the input image 230 is taken, among others.

In applying the input image 230, the parameter selector 145 may input or feed the image 230 (or the corresponding feature space representation) into the parameter selection model 155. In some embodiments, the parameter selector 145 may apply the input data 235 in addition with the input image 230 into the parameter selection model 155. The parameter selector 145 may also apply the weights or parameters of the parameter selection model 155 to generate and output the treatment parameters for the recommended treatment. From applying the weights or parameters of the parameter selection model 155, the parameter selector 145 may identify or select the one or more values from a set of candidate values for the treatment parameters of the recommended treatment. In selecting the values, the parameter selector 145 may compare the input image 230 with the sample image 170 (or the corresponding feature space representations) used to train the parameter selection model 155. Based on the comparison, the parameter selector 145 may select or identify at least of the sample images 170 used to train the parameter selection model 155. For example, the treatment selection model 155 maybe a clustering model, and the parameter selector 145 may select the sample image 170 closest to the input image 230 in the feature space representation. With the identification, the parameter selector 145 may identify the values of the treatment parameters from the label 175 of the example 165 corresponding to the sample image 170. Continuing from the previous example, once the sample image 170 closest to the input image 230 is found, the parameter selector 145 may identify the one or more values of the treatment parameters from the label 175 in the example 165 that is associated with the sample image 170. The treatment parameters may include, for example: a type or modality of treatment; a distance between an applicator of the treatment and the skin lesion in the image 230; an energy, force, or pressure to be applied via the applicator to the skin lesion in administering the treatment; a time duration of the administration of the treatment; and a frequency of administration of treatment, among others. The set of candidate values may correspond to the values in the examples 165 used to train the parameter selection model 155.

The treatment parameters identified by the parameter selector 145 may form or define one recommended treatment, and the selection of one value may affect or may be dependent on the selection of other values forming the treatment parameter. In some embodiments, from applying the input image 230 to the parameter selection model 155, the parameter selector 145 may select a value for the type of treatments from the candidate types of treatments (e.g., cryotherapy or a liquid solution-based therapies). The parameter selector 145 may select a value for each of the attributes of the applicator itself from a set of candidate attributes for the applicator (e.g., a type of applicator, a size of tip, and use of a pledget). The parameter selector 145 may select a value for the distance for the applicator from a set of candidate distances (e.g., 0.1 cm, 0.5 cm, 0.75 cm, 1 cm, 2 cm, or 5 cm). The selection of the value for the distance may depend on the selected value for the type of treatment, among others. The parameter selector 145 may select a value for the pressure to be applied from a set of candidate pressures (e.g., 2 psi, 5 psi, 10 psi, and 30 psi). The selection of the value for the pressure may depend on the selected value for the type of treatment or the value for the distance of the applicator, among others. The parameter selector 145 may select a value for the time duration in administering the treatment from a set of candidate time durations (e.g., 15 seconds, 30 seconds, 1 minutes, 3 minutes, 5 minutes, 15 minutes, and 30 minutes). The selection of the value for the time duration may depend on the selected value for the type of treatment, the value for the distance of the applicator, and the value for the time duration, among others. The parameter selector 145 may select a value for the frequency of administration of the treatment from a set of candidate frequencies (e.g., once per three days, once per week, or once per month).

In some embodiments, the parameter selector 145 may apply the input image 230 (and the input data 235) to the parameter selection model 155 to generate or output values corresponding to the treatment parameters for a set of recommended treatments. Each of the recommended treatments may be defined by the one or more values corresponding to the treatment parameters selected using the parameter selection model 155 as detailed above. In addition, the parameter selector 145 may apply the parameter selection model 155 to the input image 230 to generate or output a value corresponding to a likelihood of success of the recommended treatment. The value may be determined from application of the weights or parameters of the parameter selection model 155 to the inputs. The likelihood of success may represent a probability that the recommended treatment is to succeed (or fail) at remedying the skin lesion in the input image 230.

In some embodiments, the parameter selector 145 may rank the set of recommended treatments by the corresponding likelihoods of success. The parameter selector 145 may remove a subset of the recommended treatments from the set based on the likelihoods of success. For each treatment in the initial set of recommended treatments, the parameter selector 145 may compare the likelihood of success of the treatment to a threshold likelihood. The threshold likelihood may correspond to a value at which to include or exclude the treatment from the final set of recommended treatments. If the likelihood of success satisfies (e.g., greater than or equal to) the threshold likelihood, the parameter selector 145 may include the corresponding recommended treatment in the final set. Otherwise, if the likelihood of success does not satisfy (e.g., less than) the threshold likelihood, the parameter selector 145 may exclude the recommended treatment from the final set.

Upon output, the parameter selector 145 may associate the input image with the one or more recommended treatments generated using the parameter selection model 155. In addition, the parameter selector 145 may store and maintain an association between the input image 230 and the one or more recommended treatments generated using the parameter selection model 155. The association may be maintained and stored on a database, and may correspond to at least one data structure or entry relating the treatment parameters of each recommended treatment to the input image 230. In some embodiments, the parameter selector 145 may associate the subject identifier corresponding to the subject 220 with the input image 230 and the treatment parameters of the recommended treatment.

The parameter selector 145 may transmit or provide at least one output 240 to one of the clients 110. The output 240 may be generated using the association maintained on the database. The output 240 may indicate, identify, or include the values for the treatment parameters of the recommended treatments for the skin lesion in the input image 230 taken from the subject 220. The output 240 may include at least one message identifying the values of the treatment parameters of the recommended treatments for presentation at the client 110. The message may include instructions (e.g., for a prompt) to present the values of the treatment parameters of the recommended treatment. In some embodiments, the output 240 may be provided upon receipt of the request for the recommendation from the client 110 as discussed above. The parameter selector 145 may identify the association corresponding to the subject identifier of the subject 220 included in the request. Using the identified association, the parameter selector 145 may generate the output 240 to provide to the client 110.

With the provision of the output 240, the client 110 may present the values of the treatment parameters of the one or more recommended treatments outputted by the parameter selection model 155. For example, an application running on the client 110 may display a graphical user interface (e.g., a prompt) that contains the values corresponding to treatment parameters for the recommended treatment. Viewing the output 240 on the client 110, the clinician 225 (e.g., a medical professional) may apply a treatment 245 on the subject 220 in accordance with one of the recommended treatments. For example, the recommended treatment of the output 240 may specify use of liquefied nitrous oxide using an applicator at 2.5 cm away from the skin lesion on the region of the outer skin on the subject 220. Using the output 240, the clinician 225 may find an application tool filled with liquefied nitrous oxide to administer the treatment 245 on the skin lesion of the subject 220 at approximately 2.5 cm away from the affected region containing the skin lesion.

At a subsequent time, the clinician 225 may examine the region on the outer skin of the clinician 225 upon which the treatment 245 was administered. By examining, the clinician 225 may decide whether the treatment 245 applied on the skin lesion was successful or failed. Using the application running on the client 110, the clinician 225 may input a result of the administration of the treatment 245 on the subject 225. The result may indicate whether the treatment 245 administered in accordance with one of the recommended treatments is successful or a failure. The result may also identify the recommended treatment corresponding to the treatment 245 administered to the subject 225. The client 110 may provide the result to the parameter selection system 105.

Upon receipt, the model trainer 130 may identify the result from the client 110 to determine whether the recommended treatment corresponding to the treatment 245 administered to the subject 225 is successful. Based on the result, the model trainer 130 may update the parameter selection model 155. In some embodiments, the model trainer 130 may adjust, set, or change, at least one weight or parameter of the parameter selection model 155, when the result indicates that the recommended treatment failed. For example, the model trainer 130 may calculate an error measure (e.g., mean squared error) representing the failure of the recommended treatment corresponding to the treatment 245 administered to the subject 220. The model trainer 130 may use the error measure to change values of the weights or parameters in the parameter selection model 155.

In this manner, the parameter selection system 105 may reduce or eliminate the reliance on special expertise to diagnose and treat skin lesions on human subject, and may lessen the time of the overall process. Furthermore, the parameter selection system 105 may decrease the dependency on invasive diagnosis methods, such as a skin biopsy with a needle. By using models to perform the diagnosis and generate recommended treatments, the parameter selection system 105 may produce a more objective and accurate measures. Moreover, the functionality of the diagnosis and treatment selection of skin lesions may be distributed across several devices at various locations.

Figure 3A:
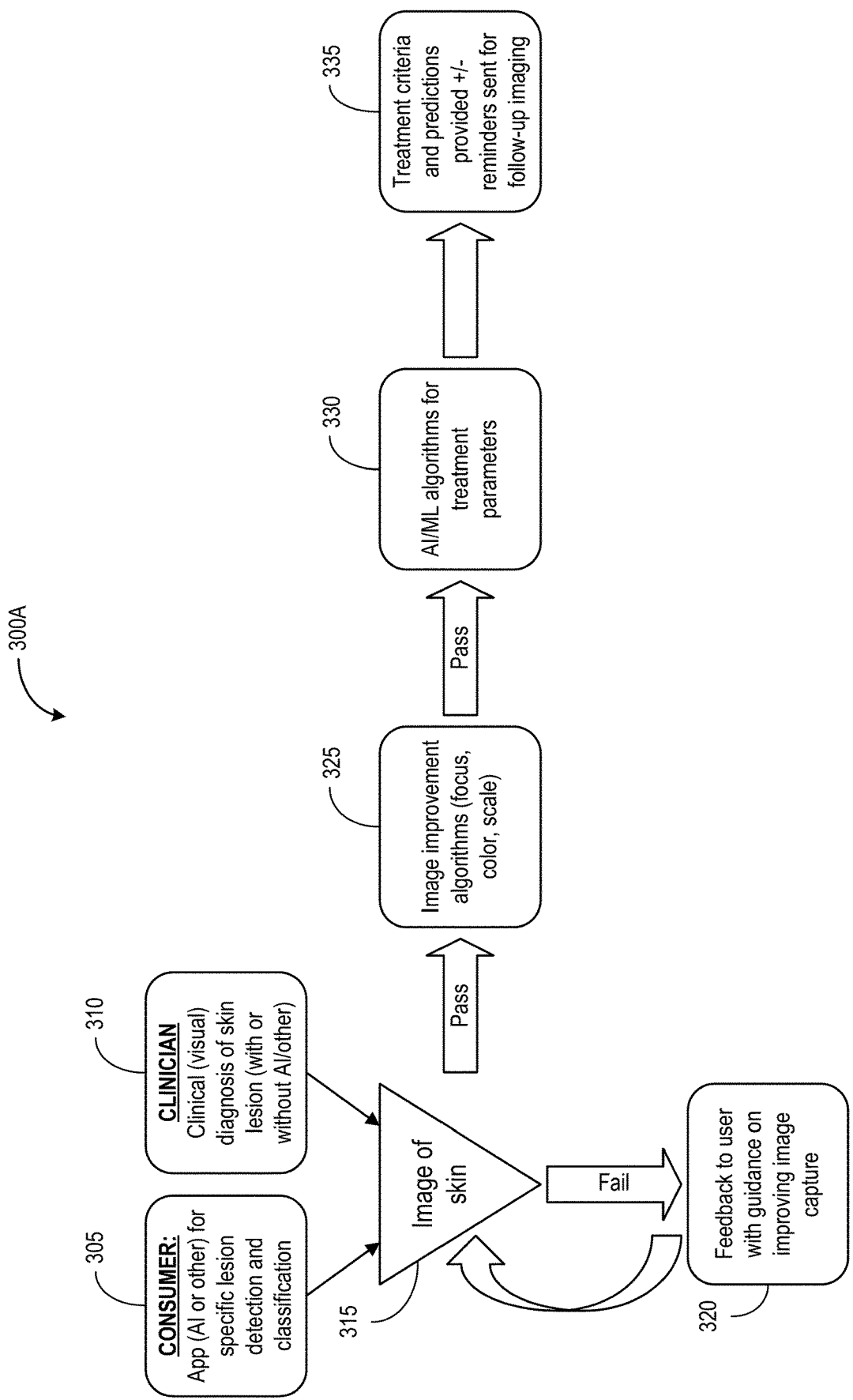
FIGS. 3A-3C each depict sequence diagrams of an example process for selecting treatment parameters values for treating skin lesions in accordance with an illustrative embodiment.

Referring now to FIG. 3A, depicted is a sequence diagram of a processes 300A for selecting treatment parameters values for treating skin lesions. The process 300A may be implemented or performed using any of the components described herein in conjunction with FIGS. 1 and 2 above or FIG. 5 below. Under process 300A, an application running on the client may be used to detect and classify specific skin lesions on the subject (305). The clinician may also make a separate, visual diagnosis of the skin lesion (310). The image of the skin may be used to determine whether the image contains a skin lesion (315). When the image is determined to not contain any skin lesion, feedback may be provided to the user with guidance on reacquiring the image (320). Otherwise, when the image is determined to contain a skin lesion, image may be pre-processed to improve (e.g., focus, color, and scale) (325). Machine learning algorithms or models may be applied to generate treatment parameters (330). Treatment criteria and predictions may be provided along with reminders for follow-up imaging (335).

Figure 3B:
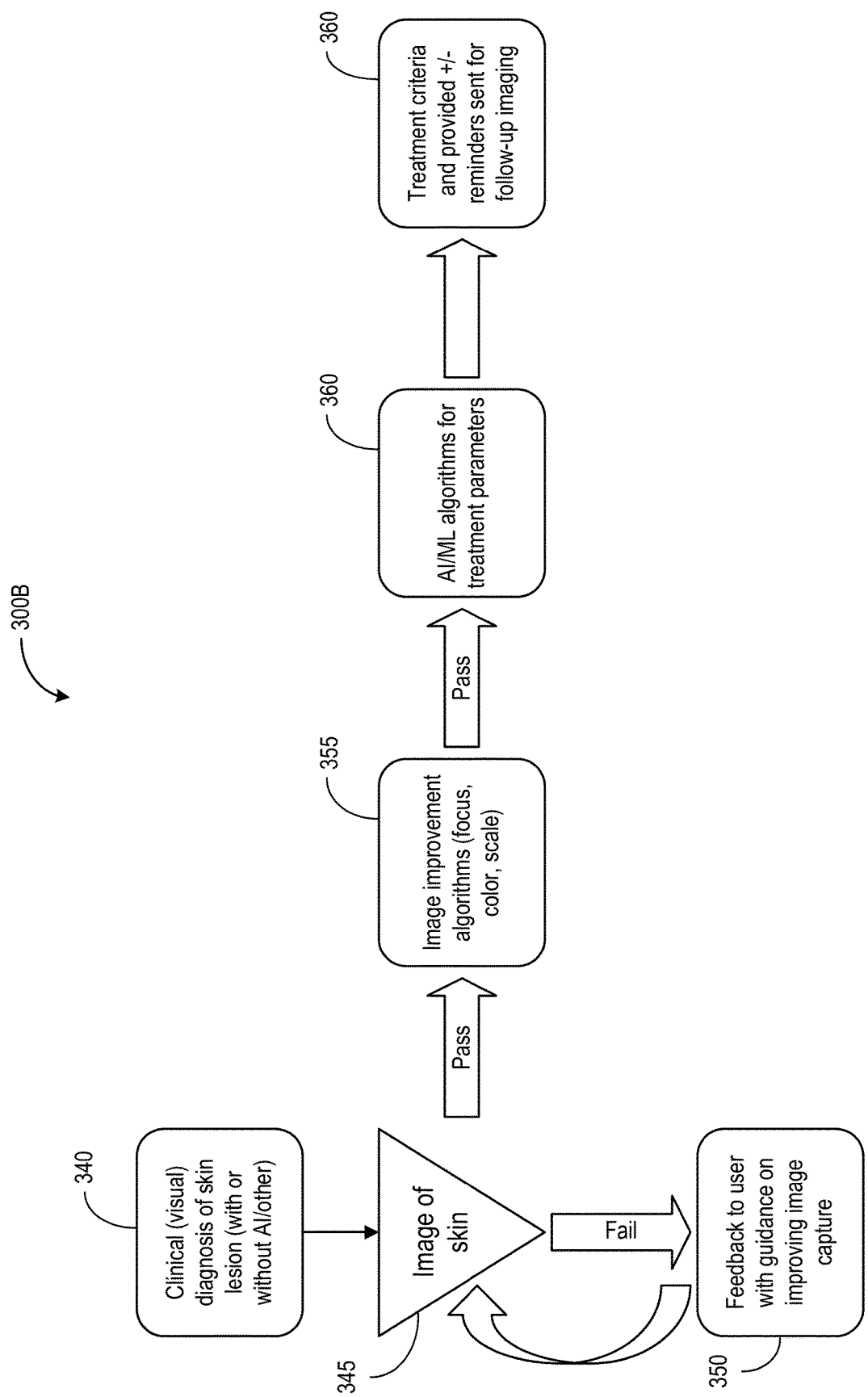

Referring now to FIG. 3B, depicted is a sequence diagram of a processes 300B for selecting treatment parameters values for treating skin lesions. Process 300B may be implemented or performed using any of the components described herein in conjunction with FIGS. 1 and 2 above or FIG. 5 below. Process 300B may be similar to process 300A, but focuses on the use of the system 100 by the clinician 225. Under process 300B, a clinician may also make a visual diagnosis of the skin lesion (340). The image of the skin may be used to determine whether the image contains a skin lesion (345). When the image is determined to not contain any skin lesion, feedback may be provided to the user with guidance on reacquiring the image (350). Otherwise, when the image is determined to contain a skin lesion, image may be pre-processed to improve (e.g., focus, color, and scale) (355). Machine learning algorithms or models may be applied to generate treatment parameters (360). Treatment criteria and predictions may be provided along with reminders for follow-up imaging (365).

Figure 3C:
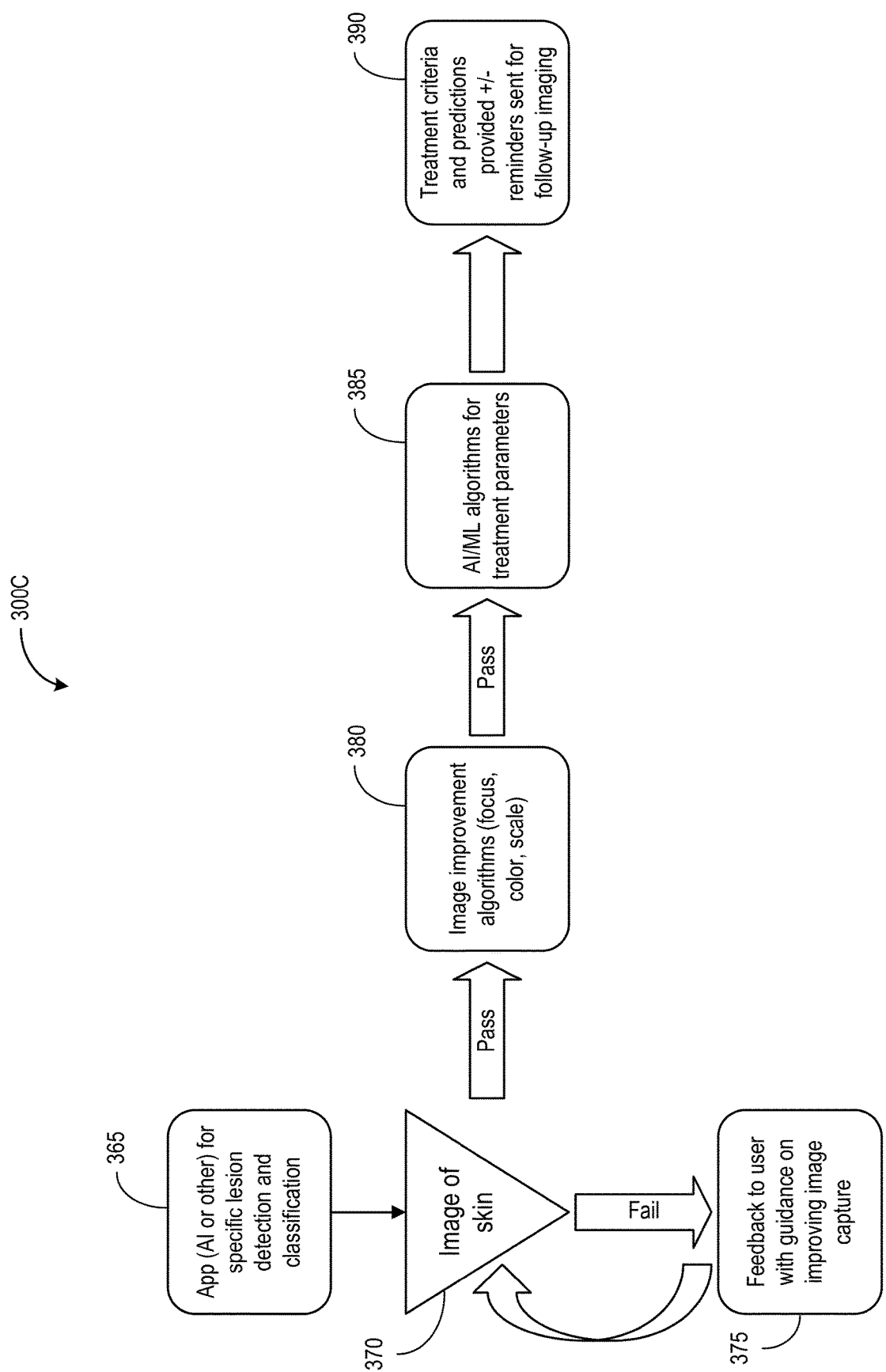

Referring now to FIG. 3C, depicted is a sequence diagram of a processes 300C for selecting treatment parameters values for treating skin lesions. Process 300C may be implemented or performed using any of the components described herein in conjunction with FIGS. 1 and 2 above or FIG. 5 below. Process 300C may be similar to process 300A, but focuses on the use of the system 100 by the subject 220 or another user besides the clinician 225. Under process 300C, an application running on the client may be used to detect and classify specific skin lesions on the subject (365). The image of the skin may be used to determine whether the image contains a skin lesion (370). When the image is determined to not contain any skin lesion, feedback may be provided to the user with guidance on reacquiring the image (375). Otherwise, when the image is determined to contain a skin lesion, image may be pre-processed to improve (e.g., focus, color, and scale) (380). Machine learning algorithms or models may be applied to generate treatment parameters (385). Treatment criteria and predictions may be provided along with reminders for follow-up imaging (390).

Figure 4:
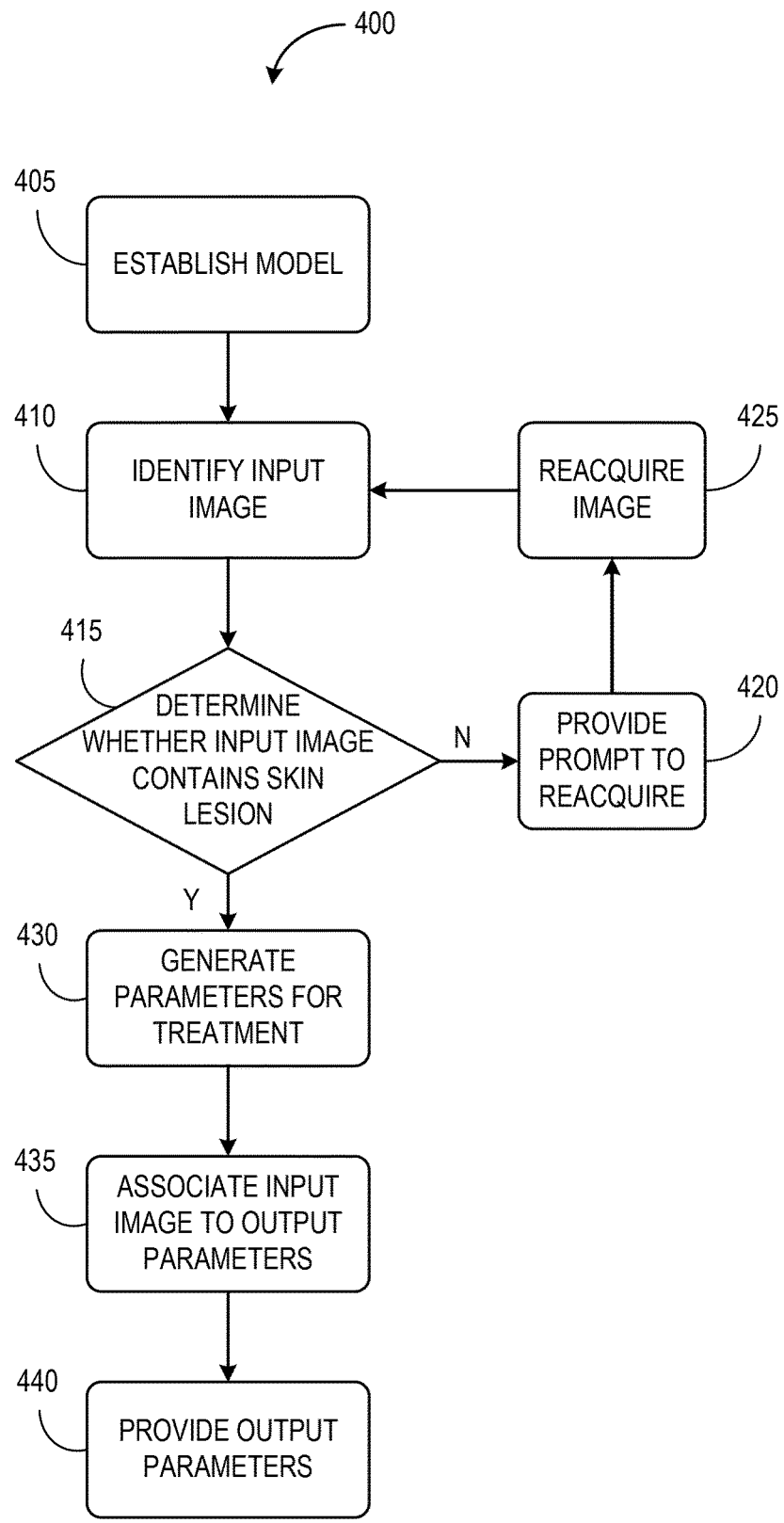
FIG. 4 depicts a flow diagram of an example method of selecting treatment parameters values for treating skin lesions in accordance with an illustrative embodiment.

Referring now to FIG. 4, depicted is a flow diagram of a method 400 of selecting treatment parameters values for treating skin lesions. The method 400 may be implemented or performed using any of the components described herein in conjunction with FIGS. 1-3C above or FIG. 5 below. In overview, a computing device may establish a model (405). The computing device may identify an input image (410). The computing device may determine whether the input image contains a skin lesion (415). If the input image is determined to not contain a skin lesion, the computing device may provide a prompt to reacquire (420). The computing device may also reacquire the image (425). Otherwise, if the input image is determined to contain a skin lesion, the computing device may generate parameters for treatment (430). The computing device may associate input image to the output parameters (435). The computing device may provide the output parameters (440).

In further detail, a computing device (e.g., parameter selection system 105) may establish at least one model (e.g., the feature recognition model 150 or the parameter selection model 155) (405). One model may be to detect the presence of a skin condition (e.g., seborrheic keratosis) in an image of an outer skin based on visual characteristics of the image. To establish the model, the computing device may use training data with sample images of skin labeled as having or not having the skin condition on the outer skin. With the sample images and the labels in the training data, the computing device may train the model until convergence is reached. Another model may be to generate a recommended treatment to administer to the skin condition identified in the image of the outer skin. In establishing the model, the computing device may use training data. The training data may include example images of skin with labels associated the treatment applied to the skin condition (e.g., the skin lesion 215) on the skin. The labels may include, for example: an indication of success or failure in the treatment; treatment parameters such as type of treatment, a distance between applicator and the skin condition, and time duration of the application, among others; traits of the subject; and an anatomical location from which the image of the skin condition is taken, among others. Using the examples of the training data, the computing device may train the model until convergence is reached.

The computing device may identify an input image (e.g., the input image 230) (410). The computing device may receive the input image from an image acquisition device (e.g., the image acquirer 115 or the client 110). The image acquisition device may obtain and generate the input image of a region of an outer skin of a subject (e.g., the subject 220). The user operating the image acquisition device may be the subject, a clinician (e.g., the clinician 225), or another user besides the subject or the clinician. The region of the outer skin corresponding to the input image may contain the skin condition. Once obtained, the image acquisition device may transmit or provide the input image to the computing device. With receipt, the computing device may perform pre-processing on the input image for input to the model.

The computing device may determine whether the input image contains a skin lesion (415). The computing device may apply the input image to the model to determine whether the input image contains the skin lesions based on visual characteristics of the model. Once fed and processed, the model may output an indication identifying whether the region of the outer skin corresponding to the input image contains the skin lesion. If the input image is determined to not contain a skin lesion, the computing device may provide a prompt to reacquire (420). The computing device may transmit a message for the prompt to reacquire the image of the skin condition. The message may include feedback specifying a correction to reacquire the image. The computing device may also reacquire the image (425), and may repeat the functions of (410) and (415).

Otherwise, if the input image is determined to contain a skin lesion, the computing device may generate parameters for treatment (430). The computing device may apply the input image to the model to generate values identifying treatment parameters for a recommended treatment. In addition to the input image, the computing device may also apply input data (e.g., the input data 235) containing additional information about the subject and the skin condition to the model. In applying the model, the computing device may select values from a set of candidate values of treatment parameters for the recommended treatment. The set of candidate values may include, for example, a type of treatment; a distance between an applicator of the treatment and the skin condition; and a time duration of the administration of the treatment, among others. The selection of one value for the treatment parameter may depend on the selection of another value. The values for the treatment parameters may form the recommended treatment for the skin condition identified in the region of the outer skin from which the image is obtained. In addition, the computing device may use the model to determine a likelihood of success (or failure) in the recommended treatment.

The computing device may associate input image to the output parameters (435). With the generation of the treatment parameters, the computing device may associate the input image from the subject to the values of the parameters for the recommended treatment. The computing device may also associate a subject identifier for the subject with the values of the treatment parameters and the input image. The computing device may store and maintain the association of the treatment parameters, the input image, and the subject identifier, among others, on a database. The association may be maintained on the database as a data structure or an entry.

The computing device may provide the output parameters (e.g., the output 240) (440). The computing device may transmit the output parameters of the recommended treatment to a client (e.g., the client 110) for presentation on the client. An application running on the client may display information corresponding to values of treatment parameters of the recommended treatment. Using the information, the clinician may administer a treatment (e.g., the treatment 245) to the skin condition of the subject. The clinician may also input a result of the treatment administered in accordance with the values of the treatment parameters on the client to send the result to the computing device. Using the result, the computing device may update or change the model for generated recommended treatments.

B. Computing and Network Environment

Figure 5:
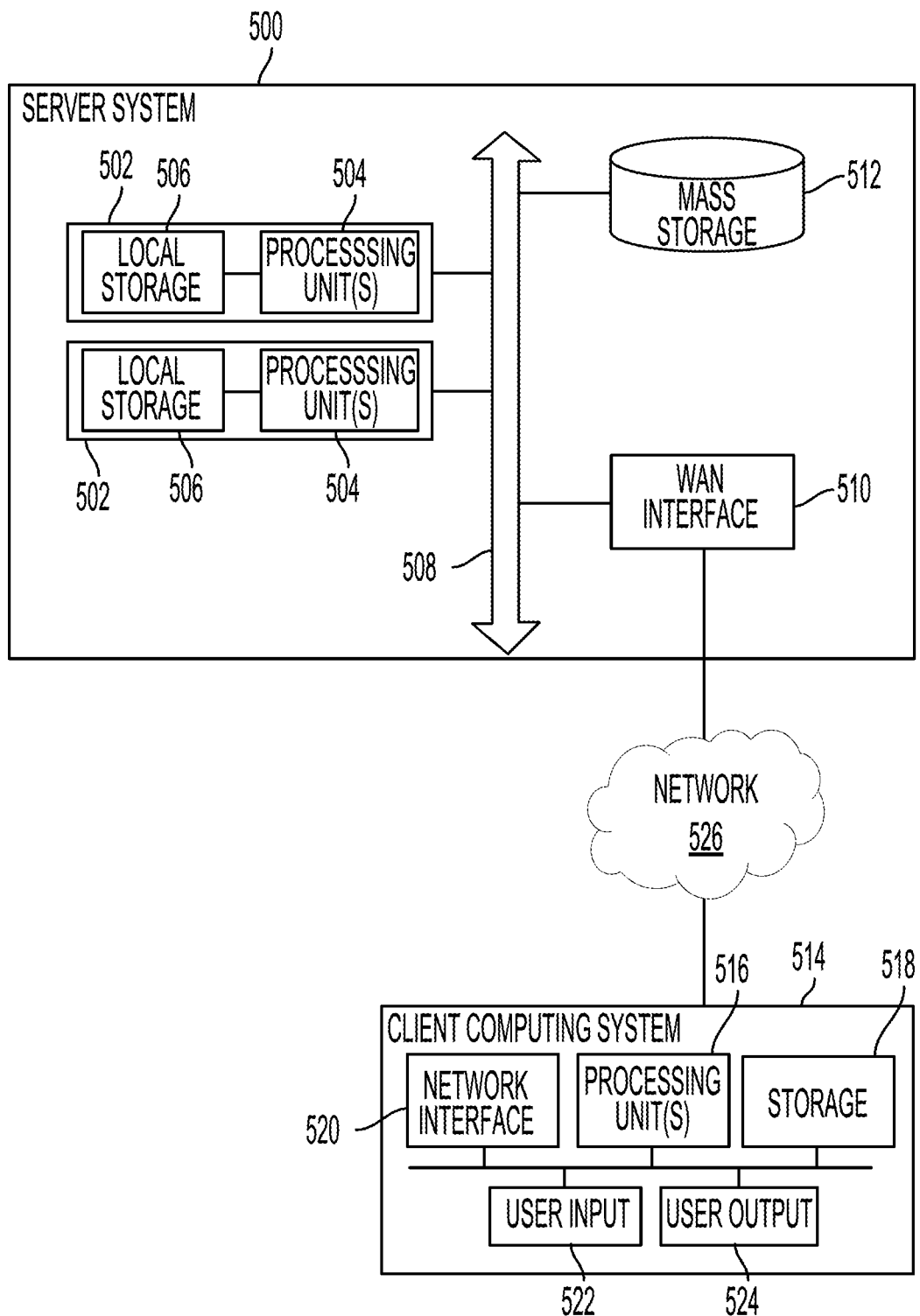
FIG. 5 depicts a block diagram of a server system and a client computer system in accordance with an illustrative embodiment.

Various operations described herein can be implemented on computer systems. FIG. 5 shows a simplified block diagram of a representative server system 500, client computer system 514, and network 526 usable to implement certain embodiments of the present disclosure. In various embodiments, server system 500 or similar systems can implement services or servers described herein or portions thereof. Client computer system 514 or similar systems can implement clients described herein. The system 100 (e.g., the parameter selection system 105) and others described herein can be similar to the server system 500.

Server system 500 can have a modular design that incorporates a number of modules 502 (e.g., blades in a blade server embodiment); while two modules 502 are shown, any number can be provided. Each module 502 can include processing unit(s) 504 and local storage 506.

Processing unit(s) 504 can include a single processor, which can have one or more cores, or multiple processors. In some embodiments, processing unit(s) 504 can include a general-purpose primary processor as well as one or more special-purpose co-processors such as graphics processors, digital signal processors, or the like. In some embodiments, some or all processing units 504 can be implemented using customized circuits, such as application specific integrated circuits (ASICs) or field programmable gate arrays (FP- GAs). In some embodiments, such integrated circuits execute instructions that are stored on the circuit itself. In other embodiments, processing unit(s) 504 can execute instructions stored in local storage 506. Any type of processors in any combination can be included in processing unit(s) 504.

Local storage 506 can include volatile storage media (e.g., DRAM, SRAM, SDRAM, or the like) and/or non-volatile storage media (e.g., magnetic or optical disk, flash memory, or the like). Storage media incorporated in local storage 506 can be fixed, removable or upgradeable as desired. Local storage 506 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 504 need at runtime. The ROM can store static data and instructions that are needed by processing unit(s) 504. The permanent storage device can be a non-volatile read-and-write memory device that can store instructions and data even when module 502 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 506 can store one or more software programs to be executed by processing unit(s) 504, such as an operating system and/or programs implementing various server functions such as functions of the parameter selection system 105 of FIG. 1 or any other system described herein, or any other server(s) associated with the parameter selection system 105 or any other system described herein.

"Software" refers generally to sequences of instructions that, when executed by processing unit(s) 504 cause server system 500 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 504. Software can be implemented as a single program or a collection of separate programs or program modules that interact as desired. From local storage 506 (or non-local storage described below), processing unit(s) 504 can retrieve program instructions to execute and data to process in order to execute various operations described above.

In some server systems 500, multiple modules 502 can be interconnected via a bus or other interconnect 508, forming a local area network that supports communication between modules 502 and other components of server system 500. Interconnect 508 can be implemented using various technologies including server racks, hubs, routers, etc.

A wide area network (WAN) interface 510 can provide data communication capability between the local area network (interconnect 508) and the network 526, such as the Internet. Technologies can be used, including wired (e.g., Ethernet, IEEE 802.3 standards) and/or wireless technologies (e.g., Wi-Fi, IEEE 802.11 standards).

In some embodiments, local storage 506 is intended to provide working memory for processing unit(s) 504, providing fast access to programs and/or data to be processed while reducing traffic on interconnect 508. Storage for larger quantities of data can be provided on the local area network by one or more mass storage subsystems 512 that can be connected to interconnect 508. Mass storage subsystem 512 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 512. In some embodiments, additional data storage resources may be accessible via WAN interface 510 (potentially with increased latency).

Server system 500 can operate in response to requests received via WAN interface 510. For example, one of modules 502 can implement a supervisory function and assign discrete tasks to other modules 502 in response to received requests. Work allocation techniques can be used. As requests are processed, results can be returned to the requester via WAN interface 510. Such operation can generally be automated. Further, in some embodiments, WAN interface 510 can connect multiple server systems 500 to each other, providing scalable systems capable of managing high volumes of activity. Techniques for managing server systems and server farms (collections of server systems that cooperate) can be used, including dynamic resource allocation and reallocation.

Server system 500 can interact with various user-owned or user-operated devices via a wide-area network such as the Internet. An example of a user-operated device is shown in FIG. 5 as client computing system 514. Client computing system 514 can be implemented, for example, as a consumer device such as a smartphone, other mobile phone, tablet computer, wearable computing device (e.g., smart watch, eyeglasses), desktop computer, laptop computer, and so on.

For example, client computing system 514 can communicate via WAN interface 510. Client computing system 514 can include computer components such as processing unit(s) 516, storage device 518, network interface 520, user input device 522, and user output device 524. Client computing system 514 can be a computing device implemented in a variety of form factors, such as a desktop computer, laptop computer, tablet computer, smartphone, other mobile computing device, wearable computing device, or the like.

Processor 516 and storage device 518 can be similar to processing unit(s) 504 and local storage 506 described above. Suitable devices can be selected based on the demands to be placed on client computing system 514; for example, client computing system 514 can be implemented as a "thin" client with limited processing capability or as a high-powered computing device. Client computing system 514 can be provisioned with program code executable by processing unit(s) 516 to enable various interactions with server system 500 of a message management service such as accessing messages, performing actions on messages, and other interactions described above. Some client computing systems 514 can also interact with a messaging service independently of the message management service.

Network interface 520 can provide a connection to the network 526, such as a wide area network (e.g., the Internet) to which WAN interface 510 of server system 500 is also connected. In various embodiments, network interface 520 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 522 can include any device (or devices) via which a user can provide signals to client computing system 514; client computing system 514 can interpret the signals as indicative of particular user requests or information. In various embodiments, user input device 522 can include any or all of a keyboard, touch pad, touch screen, mouse or other pointing device, scroll wheel, click wheel, dial, button, switch, keypad, microphone, and so on.

User output device 524 can include any device via which client computing system 514 can provide information to a user. For example, user output device 524 can include a display to display images generated by or delivered to client computing system 514. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 524 can be provided in addition to or instead of a display. Examples include indicator lights, speakers, tactile "display" devices, printers, and so on.

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 504 and 516 can provide various functionality for server system 500 and client computing system 514, including any of the functionality described herein as being performed by a server or client, or other functionality associated with message management services.

It will be appreciated that server system 500 and client computing system 514 are illustrative and that variations and modifications are possible. Computer systems used in connection with embodiments of the present disclosure can have other capabilities not specifically described here. Further, while server system 500 and client computing system 514 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, numerous modifications are possible. For instance, although specific examples of recommended treatments and processes for generating the recommended treatments are described, other rules and processes can be implemented. Embodiments of the disclosure can be realized using a variety of computer systems and communication technologies including but not limited to specific examples described herein.

Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method of selecting treatment parameter values for treating skin lesions, comprising:

training, by one or more processors, a treatment parameter selection model using a training dataset, the training dataset including a plurality of examples, each example including i) a sample image of an example skin lesion to which a treatment is administered using a cutaneous applicator; ii) a first label indicating an outcome corresponding to one of success or failure of the treatment applied to the example skin lesion in the sample image; and iii) a second label indicating at least one value corresponding to one or more treatment parameters defining the treatment applied to the example skin lesion, the predefined one or more treatment parameters specifying:

a type of the treatment corresponding to one of a first treatment type or a second treatment type, one or more attributes of the cutaneous applicator for the treatment, and at least one of an amount of dosage of the treatment corresponding to the first treatment type on the example skin lesion or a duration of administration of the treatment corresponding to the second treatment type on the example skin lesion, wherein the treatment parameter selection model is trained by:

iteratively inputting a respective example of the plurality of examples into the treatment parameter selection model, generating a respective output of the treatment parameter selection model, the output including i) at least one expected value corresponding to the one or more treatment parameters and ii) an expected outcome of success or failure in treating the example skin lesion using the at least one expected value, and adjusting weights of the treatment parameter selection model based on comparing the respective output to the outcome of first label and the at least one value corresponding to one or more treatment parameters of the second label in the respective example;

identifying, by the one or more processors, an input image including one or more visual characteristics;

determining, by the one or more processors, that the input image corresponds to a skin lesion based on the one or more visual characteristics of the input image;

applying, by the one or more processors, responsive to determining that the input image includes the skin lesion, the treatment parameter selection model to the input image to output one or more values corresponding to the one or more treatment parameters to define a recommended treatment to apply to the skin lesion corresponding to the input image; and storing, by the one or more processors, in one or more data structures, an association-between the input image and the one or more values corresponding to the one or more treatment parameters to define the recommended treatment to apply to the skin lesion corresponding to the input image.

2. The method of claim 1, further comprising:

determining, by the one or more processors, that a second input image does not include any skin lesions based on one or more second visual characteristics of the second input image; and providing, by the one or more processors, responsive to determining that the second input image does not include any skin lesions, a message for presentation indicating that the second input image does not include any skin lesions.

3. The method of claim 1, further comprising establishing, by the one or more processors, a feature recognition model using a second training dataset, the second training dataset including a first plurality of images and a second plurality of images, the first plurality of images identified as including at least one skin lesion, the second plurality of images identified as not including any skin lesions; and wherein determining that the input image includes the skin lesion further comprises applying the feature recognition model to the input image to determine that the input image includes the skin lesion based on the one or more visual characteristics.

4. The method of claim 1, further comprising:

receiving, by the one or more processors, a result indicating one of success or failure of the recommended treatment applied to the skin lesion included in the input image; and updating, by the one or more processors, the treatment parameter selection model using the result and the one or more values corresponding to the one or more treatment parameters for the recommended treatment.

5. The method of claim 1, wherein the predefined one or more treatment parameters further specify a distance between the cutaneous applicator of the treatment and the example skin lesion.

6. The method of claim 1, wherein at least one value outputted by the treatment parameter selection model further comprises a candidate duration selected from a plurality of candidate durations of administering the treatment on the skin lesion.

7. The method of claim 1, wherein at least one value outputted by the treatment parameter selection model further comprises a candidate type of treatment selected from a plurality of candidate types of treatments.

8. The method of claim 1, wherein training the treatment parameter selection model further comprises training the treatment parameter selection model using the training dataset, the training dataset including the plurality of examples, each example including a third label identifying one or more trait characteristics of a sample subject from which the sample image including the example skin lesion is acquired.

9. The method of claim 1, wherein applying the treatment parameter selection model further comprises applying the treatment parameter selection model to the input image to output a plurality of recommended treatments to apply to the skin lesion included in the input image, each treatment defined by one or more values corresponding to the one or more treatment parameters and associated with a likelihood of success of treating the skin lesion.

10. The method of claim 1, further comprising providing, by the one or more processors, a message for presentation identifying the one or more values corresponding to the one or more treatment parameters for the recommended treatment to apply to the skin lesion included in the input image.

11. A system for selecting treatment parameters values for treating skin lesions, comprising:

one or more processors, configured to:

train a treatment parameter selection model using a training dataset, the training dataset including a plurality of examples, each example including i) a sample image of an example skin lesion to which a treatment is administered using a cutaneous applicator; ii) a first label indicating an outcome corresponding to one of success or failure of the treatment applied to the example skin lesion in the sample image; and iii) a second label indicating at least one value corresponding to one or more treatment parameters defining the treatment applied to the example skin lesion, the predefined one or more treatment parameters specifying:

a type of the treatment corresponding to one of a first treatment type or a second treatment type, one or more the cutaneous applicator for the treatment, and at least one of an amount of the treatment corresponding to the first treatment type dispensed by the cutaneous applicator on the example skin lesion or a duration of administration of the treatment corresponding to the second treatment type on the example skin lesion;

wherein the treatment parameter selection model is trained by:
  iteratively inputting a respective example of the plurality of examples into the treatment parameter selection model,
  generating a respective output of the treatment parameter selection model, the output including i) at least one expected value corresponding to the one or more treatment parameters and ii) an expected outcome of success or failure in treating the example skin lesion using the at least one expected value, and
  adjusting weights of the treatment parameter selection model based on comparing the respective output to the outcome of first label and the at least one value corresponding to one or more treatment parameters of the second label in the respective example;
identify an input image including one or more visual characteristics;
determine that the input image includes a skin lesion based on the one or more visual characteristics of the input image;
apply, responsive to determining that the input image includes the skin lesion, the treatment parameter selection to the input image to output one or more values corresponding to the one or more treatment parameters to define a recommended treatment to apply to the skin lesion included in the input image; and
store, in one or more data structures, an association between the input image and the one or more values corresponding to the one or more treatment parameters to define the recommended treatment to apply to the skin lesion corresponding to the input image.

12. The system of claim 11, wherein the one or more processors are further configured to:
  determine that a second input image does not include any skin lesions based on one or more second visual characteristics of the second input image; and
  provide, responsive to determining that the second input image does not include any skin lesions, a message for presentation indicating that the second input image does not include any skin lesions.

13. The system of claim 11, wherein the one or more processors are further configured to:
  establish a feature recognition model using a second training dataset, the second training dataset including a first plurality of images and a second plurality of images, the first plurality of images identified as including at least one skin lesion, the second plurality of images identified as not including any skin lesions; and
  apply the skin lesion recognition to the input image to determine that the input image includes the skin lesion based on the one or more visual characteristics.

14. The system of claim 11, wherein the one or more processors are further configured to:
  receive a result indicating one of success or failure of the recommended treatment applied to the skin lesion included in the input image; and
  update the treatment parameter selection model using the result and the one or more values corresponding to the one or more treatment parameters for the recommended treatment.

15. The system of claim 11, wherein the predefined one or more treatment parameters further specify a distance between the cutaneous applicator of the treatment and the example skin lesion.

16. The system of claim 11, wherein at least one value outputted by the treatment parameter selection model further comprises a candidate duration selected from a plurality of candidate durations of administering the treatment on the skin lesion.

17. The system of claim 11, wherein at least one value outputted by the treatment parameter selection model further comprises a candidate type of treatment selected from a plurality of candidate types of treatments.

18. The system of claim 11, wherein the one or more processors are further configured to train the treatment parameter selection model using the training dataset, the training dataset including the plurality of examples, each example including a third label identifying one or more trait characteristics of a sample subject from which the sample image including the example skin lesion is acquired.

19. The system of claim 11, wherein applying the treatment parameter selection model further comprises applying the treatment parameter selection model to the input image to output a plurality of recommended treatments to apply to the skin lesion included in the input image, each treatment defined by one or more values corresponding to the one or more treatment parameters and associated with a likelihood of success of treating the skin lesion.

* * * * *